US009693941B2

(12) United States Patent
Barne et al.

(10) Patent No.: US 9,693,941 B2
(45) Date of Patent: Jul. 4, 2017

(54) LIQUID PERSONAL WASH COMPOSITION

(71) Applicant: Conopco, Inc., Englewood Cliffs, NJ (US)

(72) Inventors: Sameer Keshav Barne, Bangalore (IN); Amit Chakrabortty, Bangalore (IN); Maya Treesa Saji, Bangalore (IN)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 14/354,406

(22) PCT Filed: Oct. 15, 2012

(86) PCT No.: PCT/EP2012/070369
§ 371 (c)(1),
(2) Date: Apr. 25, 2014

(87) PCT Pub. No.: WO2013/064360
PCT Pub. Date: May 10, 2013

(65) Prior Publication Data
US 2014/0311515 A1 Oct. 23, 2014

(30) Foreign Application Priority Data
Nov. 3, 2011 (IN) .................. 3096/MUM/2011

(51) Int. Cl.
*A61K 8/362* (2006.01)
*A61K 8/34* (2006.01)
*A61K 8/365* (2006.01)
*A61Q 17/00* (2006.01)
*A61Q 19/10* (2006.01)

(52) U.S. Cl.
CPC ............... *A61K 8/362* (2013.01); *A61K 8/34* (2013.01); *A61K 8/347* (2013.01); *A61K 8/365* (2013.01); *A61Q 17/005* (2013.01); *A61Q 19/10* (2013.01)

(58) Field of Classification Search
None
See application file for complete search history.

(56) References Cited

U.S. PATENT DOCUMENTS

| 658,596 | A | 9/1900 | Simpson |
|---|---|---|---|
| 2,196,763 | A | 4/1940 | Figg, Jr. |
| 2,359,241 | A | 9/1944 | Partansky |
| 3,120,469 | A | 2/1964 | Tamas |
| 3,256,310 | A | 6/1966 | Weil |
| 3,779,932 | A | 12/1973 | Jaggers et al. |
| 3,787,566 | A | 1/1974 | Gauvreau |
| RE28,263 | E | 12/1974 | Gauvreau et al. |
| 3,966,627 | A | 6/1976 | Gray |
| 4,152,272 | A | 5/1979 | Young |
| 4,267,168 | A | 5/1981 | Van Leuven |
| 4,284,434 | A | 8/1981 | Lingmann et al. |
| 4,321,164 | A | 3/1982 | Sprecker et al. |
| 4,474,798 | A | 10/1984 | Inagi et al. |
| 4,548,809 | A | 10/1985 | Fung |
| 4,597,887 | A | 7/1986 | Colodney et al. |
| 4,645,662 | A | 2/1987 | Nakashima et al. |
| 4,900,721 | A | 2/1990 | Bansemir et al. |
| 4,966,754 | A | 10/1990 | Purohit |
| 4,992,259 | A | 2/1991 | Schiraldi et al. |
| 5,013,486 | A | 5/1991 | Joshi |
| 5,073,366 | A | 12/1991 | Beck |
| 5,110,832 | A | 5/1992 | Chastain et al. |
| 5,230,897 | A | 7/1993 | Griffin et al. |
| 5,238,056 | A | 8/1993 | Scotti et al. |
| 5,283,056 | A | 2/1994 | Chung et al. |
| 5,308,873 | A | 5/1994 | Chastain et al. |
| 5,322,638 | A | 6/1994 | Schadt et al. |
| 5,328,682 | A | 7/1994 | Pullen et al. |
| 5,435,935 | A | 7/1995 | Kupneski |
| 5,472,684 | A | 12/1995 | Nabi |
| 5,474,712 | A | 12/1995 | Dotolo |
| 5,474,761 | A | 12/1995 | Liang |
| 5,531,982 | A | 7/1996 | Gaffar et al. |
| 5,591,708 | A | 1/1997 | Richter |
| 5,610,189 | A | 3/1997 | Whiteley |
| 5,763,468 | A | 6/1998 | Barranx et al. |
| 5,817,295 | A | 10/1998 | Chaudhari et al. |
| 5,939,050 | A | 8/1999 | Iyer |
| 5,942,478 | A | 8/1999 | Lopes |
| 5,965,518 | A | 10/1999 | Nakatsu et al. |
| 6,048,368 | A | 4/2000 | Tcheou et al. |
| 6,048,836 | A | 4/2000 | Romano et al. |

(Continued)

FOREIGN PATENT DOCUMENTS

| CH | 692411 | 6/2002 |
|---|---|---|
| CN | 1669576 A | 9/2005 |

(Continued)

OTHER PUBLICATIONS

Biologically Active Substances of Plant Origin, Russian Academy of Sciences, 2001, RU.
ACHI, Composition and Antibacterial Activities of Tetrapleura tetraptera Taub, Research Journal Microbiology, 2006, 416-422, vol. 1 No. 5, US.
Banayeva, A Study of the Chemical Composition of the Essential Oil of Representatives, Vegetable feed chemistry, 1999, 41-48, 3, RU.
Banayeva, The study of the chemical composition of an essential oil, Vegetable feed chemistry, 1999, 41-48 No. 3, RU.

(Continued)

*Primary Examiner* — David J Blanchard
*Assistant Examiner* — Sarah Chickos
(74) *Attorney, Agent, or Firm* — Ronald A. Koatz

(57) ABSTRACT

The invention relates to a liquid personal cleaning composition. The present inventors have found that inclusion selected di or tricarboxylic acid or a salt thereof, when combined with thymol or terpineol provide synergistic antimicrobial action in a rapid fashion and such efficacy is very low concentrations of thymol and/or terpineol.

7 Claims, No Drawings

(56) References Cited

U.S. PATENT DOCUMENTS

| | | |
|---|---|---|
| 6,066,674 A | 5/2000 | Hioki |
| 6,103,683 A | 8/2000 | Romano et al. |
| 6,110,883 A | 8/2000 | Petri et al. |
| 6,114,298 A | 9/2000 | Petri |
| 6,177,388 B1 | 1/2001 | Cheung et al. |
| 6,183,766 B1 | 2/2001 | Sine et al. |
| 6,190,674 B1 | 2/2001 | Beerse et al. |
| 6,210,695 B1 | 4/2001 | Beerse et al. |
| 6,261,540 B1 | 7/2001 | Nelson |
| 6,277,805 B1 | 8/2001 | Kupneski |
| 6,323,166 B1 | 11/2001 | Kamiya |
| 6,455,086 B1 | 9/2002 | Trinh et al. |
| 6,458,753 B1 | 10/2002 | Haylett |
| 6,506,707 B1 | 1/2003 | Bessette |
| 6,521,578 B1 | 2/2003 | Stute et al. |
| 6,531,115 B1 | 3/2003 | Singh |
| 6,534,042 B2 | 3/2003 | Delli Santi et al. |
| 6,537,955 B1 | 3/2003 | Raso et al. |
| 6,576,247 B1 | 6/2003 | Ikemoto et al. |
| 6,585,961 B1 | 7/2003 | Stockel |
| 6,607,733 B1 | 8/2003 | Diec |
| 6,613,728 B1 | 9/2003 | Sirianni et al. |
| 6,624,126 B1 | 9/2003 | Kasuga |
| 6,645,472 B1 | 11/2003 | Anderson |
| 6,730,643 B2 | 5/2004 | Chokappa et al. |
| 6,753,305 B2 | 6/2004 | Raso et al. |
| 6,861,402 B1 | 3/2005 | Miracle |
| 6,902,726 B1 | 6/2005 | Varel |
| 6,921,745 B2 | 7/2005 | Yamada et al. |
| 7,754,774 B2 | 7/2010 | Kobayashi et al. |
| 8,066,979 B1 | 11/2011 | Dickens |
| 8,992,901 B2 | 3/2015 | Barne et al. |
| 2001/0000029 A1 | 3/2001 | Misumi |
| 2002/0002124 A1 | 1/2002 | Biedermann et al. |
| 2002/0081270 A1 | 6/2002 | Delli Santi |
| 2002/0107287 A1 | 8/2002 | Bessette et al. |
| 2002/0173436 A1 | 11/2002 | Sonnenberg et al. |
| 2002/0176879 A1 | 11/2002 | Dodd et al. |
| 2002/0182268 A1 | 12/2002 | Bessette et al. |
| 2003/0044441 A1 | 3/2003 | Schmid et al. |
| 2003/0044469 A1 | 3/2003 | Viladot Petit et al. |
| 2003/0077233 A1 | 4/2003 | Zuckerman |
| 2003/0083212 A1 | 5/2003 | Willard et al. |
| 2003/0091657 A1 | 5/2003 | Chiasson |
| 2003/0096722 A1 | 5/2003 | Caselli et al. |
| 2003/0129150 A1 | 7/2003 | Pauly et al. |
| 2003/0138394 A1 | 7/2003 | Charrouf et al. |
| 2003/0138502 A1 | 7/2003 | Pauly et al. |
| 2003/0147963 A1 | 8/2003 | De Moragas et al. |
| 2003/0152536 A1 | 8/2003 | Pauly et al. |
| 2003/0231978 A1 | 12/2003 | Franklin et al. |
| 2004/0014818 A1 | 1/2004 | Boeck et al. |
| 2004/0024020 A1 | 2/2004 | Holwerda et al. |
| 2004/0028697 A1 | 2/2004 | Pauly et al. |
| 2004/0042996 A1 | 3/2004 | Pauly et al. |
| 2004/0044078 A1 | 3/2004 | Kawa et al. |
| 2004/0047832 A1 | 3/2004 | Pauly et al. |
| 2004/0063601 A1 | 4/2004 | Denome et al. |
| 2004/0067203 A1 | 4/2004 | Parikh |
| 2004/0081714 A1 | 4/2004 | Pauly et al. |
| 2004/0096479 A1 | 5/2004 | Levine |
| 2004/0105836 A1 | 6/2004 | Seipel et al. |
| 2004/0115158 A1 | 6/2004 | Schieferstein et al. |
| 2004/0142007 A1 | 7/2004 | Moussou et al. |
| 2004/0170581 A1 | 9/2004 | Henry et al. |
| 2004/0185071 A1 | 9/2004 | Hatazaki |
| 2004/0191190 A1 | 9/2004 | Pauly et al. |
| 2004/0198630 A1 | 10/2004 | Schmid et al. |
| 2004/0209795 A1 | 10/2004 | Vlad |
| 2004/0234480 A1 | 11/2004 | Pauly et al. |
| 2005/0014827 A1 | 1/2005 | Schur |
| 2005/0019353 A1 | 1/2005 | Prinz et al. |
| 2005/0019431 A1 | 1/2005 | Modak et al. |
| 2005/0065055 A1 | 3/2005 | Barnes |
| 2005/0077497 A1 | 4/2005 | Anderson |
| 2005/0089497 A1 | 4/2005 | Prinz et al. |
| 2005/0089499 A1 | 4/2005 | Moussou et al. |
| 2005/0119153 A1 | 6/2005 | Burt et al. |
| 2005/0143277 A1 | 6/2005 | Dufay et al. |
| 2005/0172859 A1 | 8/2005 | Nieendick et al. |
| 2005/0184275 A1 | 8/2005 | Mora-Gutierrez et al. |
| 2005/0233930 A1 | 10/2005 | Cheung et al. |
| 2005/0256021 A1 | 11/2005 | Lu |
| 2006/0008482 A1 | 1/2006 | Prinz et al. |
| 2006/0034880 A1 | 2/2006 | Christmas et al. |
| 2006/0039956 A1 | 2/2006 | Hensen et al. |
| 2006/0040847 A1 | 2/2006 | Weibel |
| 2006/0045914 A1 | 3/2006 | Narayanan |
| 2006/0057090 A1 | 3/2006 | Buchwald-Werner |
| 2006/0079414 A1 | 4/2006 | Nieendick et al. |
| 2006/0093570 A1 | 5/2006 | Duddington et al. |
| 2006/0128585 A1 | 6/2006 | Adair et al. |
| 2006/0134013 A1 | 6/2006 | Sharma |
| 2006/0141073 A1 | 6/2006 | Worrell |
| 2006/0153959 A1 | 7/2006 | Behan et al. |
| 2006/0165631 A1 | 7/2006 | Danoux et al. |
| 2006/0165820 A1 | 7/2006 | Yatcilla |
| 2006/0270571 A1 | 11/2006 | Burke et al. |
| 2006/0276336 A1 | 12/2006 | Sardo |
| 2006/0280763 A1 | 12/2006 | Yoshida et al. |
| 2007/0014878 A1 | 1/2007 | Gardiner |
| 2007/0021319 A1 | 1/2007 | Kohle et al. |
| 2007/0053849 A1 | 3/2007 | Doyle et al. |
| 2007/0081966 A1 | 4/2007 | Behler et al. |
| 2007/0104676 A1 | 5/2007 | Moser et al. |
| 2007/0154414 A1 | 7/2007 | Bonfiglio |
| 2007/0218016 A1 | 9/2007 | Rabenhorst et al. |
| 2007/0227930 A1 | 10/2007 | Bromberg et al. |
| 2007/0231295 A1 | 10/2007 | Hoppe |
| 2007/0237847 A1 | 10/2007 | Henry et al. |
| 2007/0258991 A1 | 11/2007 | Buasen et al. |
| 2007/0258996 A1 | 11/2007 | Mookerjee et al. |
| 2007/0270321 A1 | 11/2007 | Barnhart et al. |
| 2008/0008660 A1 | 1/2008 | Rabenhorst et al. |
| 2008/0026974 A1 | 1/2008 | Barnhart et al. |
| 2008/0032908 A1 | 2/2008 | Kurtz |
| 2008/0044479 A1 | 2/2008 | Stack |
| 2008/0045491 A1 | 2/2008 | Fitchmun |
| 2008/0051312 A1 | 2/2008 | Lestage et al. |
| 2008/0064711 A1 | 3/2008 | Friedman |
| 2008/0096790 A1 | 4/2008 | Behan et al. |
| 2008/0107742 A1 | 5/2008 | Hare |
| 2008/0118591 A1 | 5/2008 | Natsch |
| 2008/0160000 A1 | 7/2008 | Motozono et al. |
| 2008/0171709 A1 | 7/2008 | Remmal |
| 2008/0194675 A1 | 8/2008 | Bettuzzi |
| 2008/0207480 A1 | 8/2008 | Pipko |
| 2008/0214432 A1 | 9/2008 | Gaudin |
| 2008/0214518 A1 | 9/2008 | Remma |
| 2008/0214568 A1 | 9/2008 | Remmal |
| 2008/0220036 A1 | 9/2008 | Miltz et al. |
| 2008/0221003 A1 | 9/2008 | Meine et al. |
| 2008/0221222 A1 | 9/2008 | Greif et al. |
| 2008/0253976 A1 | 10/2008 | Scott |
| 2008/0255247 A1 | 10/2008 | Sagalowicz et al. |
| 2008/0274072 A1 | 11/2008 | Manolas et al. |
| 2008/0299200 A1 | 12/2008 | Leser et al. |
| 2008/0299220 A1 | 12/2008 | Tamarkin et al. |
| 2009/0004308 A1 | 1/2009 | Frehner et al. |
| 2009/0035228 A1 | 2/2009 | Modak |
| 2009/0081755 A1 | 3/2009 | Schmiedel et al. |
| 2009/0105195 A1 | 4/2009 | O'Brien |
| 2009/0165228 A1 | 7/2009 | Kilkenny et al. |
| 2009/0176887 A1 | 7/2009 | Vlasaty et al. |
| 2009/0264329 A1 | 10/2009 | Underwood et al. |
| 2009/0317431 A1 | 12/2009 | Schaefer |
| 2010/0003198 A1 | 1/2010 | Stolmeier et al. |
| 2010/0047294 A1 | 2/2010 | Ahlnas |
| 2010/0061946 A1 | 3/2010 | Scherner et al. |
| 2010/0129302 A1 | 5/2010 | Ahlnas |
| 2010/0172875 A1 | 7/2010 | Phan et al. |
| 2010/0183539 A1 | 7/2010 | Bernhardt et al. |
| 2010/0184855 A1 | 7/2010 | Bernhardt et al. |
| 2011/0081528 A1 | 4/2011 | Shannon et al. |

(56) References Cited

U.S. PATENT DOCUMENTS

| | | |
|---|---|---|
| 2011/0105386 A1 | 5/2011 | Mor et al. |
| 2011/0223114 A1 | 9/2011 | Chakrabortty et al. |
| 2012/0003163 A1 | 1/2012 | Mordas et al. |
| 2012/0004641 A1 | 1/2012 | Bruehwiler et al. |
| 2012/0152149 A1 | 6/2012 | Mijolovic et al. |
| 2014/0170198 A1 | 6/2014 | Franklin et al. |
| 2014/0356230 A1 | 12/2014 | Cornmell et al. |

FOREIGN PATENT DOCUMENTS

| | | |
|---|---|---|
| CN | 101036459 | 9/2007 |
| CN | 101313772 | 12/2008 |
| CN | 101590287 A | 12/2009 |
| CN | 101601382 A | 12/2009 |
| CN | 101601382 A | 8/2010 |
| CN | 101874531 A | 11/2010 |
| CN | 102229861 | 11/2011 |
| CN | 104010500 | 12/2012 |
| DE | 2263126 | 7/1973 |
| DE | 2445676 | 4/1976 |
| DE | 3117792 | 11/1982 |
| DE | 19509079 | 9/1996 |
| DE | 102004038285 | 4/2006 |
| DE | 102004038285 A1 | 4/2006 |
| EA | EP1561476 A1 | 8/2005 |
| EP | 0112141 | 12/1983 |
| EP | 0129987 B1 | 11/1986 |
| EP | 621335 | 10/1994 |
| EP | 715856 | 6/1996 |
| EP | 0916718 A1 | 10/1997 |
| EP | 0916720 A1 | 5/1999 |
| EP | 0948892 A1 | 10/1999 |
| EP | 950399 | 10/1999 |
| EP | 0966883 A1 | 12/1999 |
| EP | 0995425 | 4/2000 |
| EP | 0995425 A2 | 4/2000 |
| EP | 1146111 | 4/2000 |
| EP | 1013261 | 6/2000 |
| EP | 1170006 | 1/2002 |
| EP | 1079703 B | 8/2002 |
| EP | 0912098 B2 | 4/2003 |
| EP | 1121411 | 12/2004 |
| EP | 1604643 | 12/2005 |
| EP | 1607098 | 12/2005 |
| EP | 1661976 | 5/2006 |
| EP | 1672054 | 6/2006 |
| EP | 1194461 | 10/2008 |
| EP | 2018869 | 1/2009 |
| EP | 2047889 | 4/2009 |
| EP | 2348838 B1 | 5/2013 |
| EP | 2787956 | 2/2016 |
| ES | 2074030 A1 | 8/1995 |
| FR | 1137 M | 5/1961 |
| FR | 861920 | 2/1962 |
| FR | 1356209 | 3/1964 |
| FR | 1356209 A | 3/1964 |
| FR | 2697133 A1 | 4/1994 |
| FR | 2752730 | 3/1998 |
| FR | 2752730 A1 | 3/1998 |
| GB | 366870 | 2/1932 |
| GB | 508407 | 6/1939 |
| GB | 741446 | 12/1955 |
| GB | 1395839 | 5/1975 |
| GB | 1420946 | 1/1976 |
| GB | 2307915 | 6/1997 |
| GB | 2319181 | 5/1998 |
| GB | 2320927 | 7/1998 |
| GB | 2322552 | 9/1998 |
| GB | 2341092 | 3/2000 |
| GB | 2354771 | 4/2001 |
| GB | 2393911 A | 4/2004 |
| JP | 47034705 | 12/1972 |
| JP | 60072801 | 4/1985 |
| JP | 61118301 | 6/1986 |
| JP | 62292709 | 12/1987 |
| JP | 2196718 | 3/1990 |
| JP | 03-011013 A2 | 1/1991 |
| JP | 8151324 | 6/1996 |
| JP | 8277371 | 10/1996 |
| JP | 8511517 | 12/1996 |
| JP | 9241139 A2 | 9/1997 |
| JP | H10114636 | 5/1998 |
| JP | 11501330 | 2/1999 |
| JP | 11502539 | 3/1999 |
| JP | 11130642 | 5/1999 |
| JP | 11228368 | 8/1999 |
| JP | 11315012 | 11/1999 |
| JP | 98044959 A1 | 1/2000 |
| JP | 2000026260 | 1/2000 |
| JP | 2000063262 | 2/2000 |
| JP | 2000508337 | 7/2000 |
| JP | 2000344641 | 12/2000 |
| JP | 2001518944 | 10/2001 |
| JP | 2001342500 | 12/2001 |
| JP | 20032809 | 1/2003 |
| JP | 200381804 | 3/2003 |
| JP | 2003113013 | 4/2003 |
| JP | 2003113013 A2 | 4/2003 |
| JP | 2003531246 | 10/2003 |
| JP | 2004075798 | 3/2004 |
| JP | 2004123674 | 4/2004 |
| JP | 2004203839 | 7/2004 |
| JP | 20052130 | 1/2005 |
| JP | 2005015368 | 1/2005 |
| JP | 2005065750 | 3/2005 |
| JP | 2005065750 A | 3/2005 |
| JP | 2005239965 | 9/2005 |
| JP | 2005298357 | 10/2005 |
| JP | 200695182 | 4/2006 |
| JP | 2006206582 | 8/2006 |
| JP | 2006307231 | 11/2006 |
| JP | 2007538062 | 12/2007 |
| JP | 2008542510 | 11/2008 |
| JP | 2009501738 | 1/2009 |
| JP | 2009516034 | 4/2009 |
| JP | 2009517447 | 4/2009 |
| JP | 2009196987 | 9/2009 |
| JP | 2009196987 A | 9/2009 |
| JP | 2009542695 | 12/2009 |
| JP | 2010037272 | 2/2010 |
| JP | 2010037272 A | 2/2010 |
| JP | 2010511037 | 4/2010 |
| JP | 201198918 | 5/2011 |
| JP | 201198921 | 5/2011 |
| JP | 2011518844 | 6/2011 |
| JP | 2012250937 A | 12/2012 |
| KR | 020030181 | 4/2002 |
| KR | 20020030181 A | 4/2002 |
| KR | 20020032949 A | 5/2002 |
| KR | 20030070487 | 8/2003 |
| KR | 100885511 | 2/2009 |
| KR | 100885511 B1 | 2/2009 |
| KR | 20100123424 A | 11/2010 |
| KR | 20120093607 A | 8/2012 |
| RU | 2228168 | 5/2004 |
| RU | 2263115 | 10/2005 |
| RU | 2277923 | 6/2006 |
| RU | 2277923 C2 | 6/2006 |
| SE | CH692411TR | 6/2002 |
| SU | 1644963 A1 | 4/1991 |
| WO | WO9218091 | 10/1992 |
| WO | WO9428714 | 12/1994 |
| WO | WO9512379 | 5/1995 |
| WO | WO9611694 | 4/1996 |
| WO | WO9623050 | 8/1996 |
| WO | WO9713495 | 4/1997 |
| WO | WO9715277 | 5/1997 |
| WO | WO9722580 | 6/1997 |
| WO | WO9725106 | 7/1997 |
| WO | WO9726855 | 7/1997 |
| WO | WO9730586 A1 | 8/1997 |
| WO | WO9731092 A1 | 8/1997 |
| WO | WO9731093 A1 | 8/1997 |
| WO | WO9801524 | 1/1998 |

(56) References Cited

FOREIGN PATENT DOCUMENTS

| | | |
|---|---|---|
| WO | WO9802044 A1 | 1/1998 |
| WO | WO9802139 | 1/1998 |
| WO | WO9811867 | 3/1998 |
| WO | WO9824314 | 6/1998 |
| WO | WO9844959 A1 | 10/1998 |
| WO | WO9854279 | 12/1998 |
| WO | WO9855080 A2 | 12/1998 |
| WO | WO9855092 | 12/1998 |
| WO | WO9855093 | 12/1998 |
| WO | WO9855094 | 12/1998 |
| WO | WO9855095 A1 | 12/1998 |
| WO | WO9855098 | 12/1998 |
| WO | WO9936033 | 7/1999 |
| WO | WO9952360 | 10/1999 |
| WO | WO9958631 | 11/1999 |
| WO | WO0000166 | 1/2000 |
| WO | WO0005964 | 2/2000 |
| WO | WO0025763 | 5/2000 |
| WO | WO0027981 | 5/2000 |
| WO | WO0051436 | 9/2000 |
| WO | WO0061106 | 10/2000 |
| WO | WO0105919 | 1/2001 |
| WO | WO0118201 | 3/2001 |
| WO | WO0121753 | 3/2001 |
| WO | WO0167868 A2 | 9/2001 |
| WO | WO0167868 A3 | 9/2001 |
| WO | WO0170215 A1 | 9/2001 |
| WO | WO0179409 A1 | 10/2001 |
| WO | WO02065859 A1 | 8/2002 |
| WO | WO02096435 | 12/2002 |
| WO | WO03010273 | 2/2003 |
| WO | WO03034994 A2 | 5/2003 |
| WO | WO03037270 A2 | 5/2003 |
| WO | WO03050224 A1 | 6/2003 |
| WO | WO03091375 | 11/2003 |
| WO | WO03095600 | 11/2003 |
| WO | W02004006679 A3 | 1/2004 |
| WO | WO2004006679 A2 | 1/2004 |
| WO | WO2004032886 A1 | 4/2004 |
| WO | WO2004035723 A1 | 4/2004 |
| WO | WO2005094385 | 10/2005 |
| WO | WO2005113128 | 12/2005 |
| WO | WO2006012715 | 2/2006 |
| WO | WO2006042661 | 4/2006 |
| WO | WO2006053458 A1 | 5/2006 |
| WO | WO2006109898 | 10/2006 |
| WO | WO2006120494 | 11/2006 |
| WO | WO2006131430 | 12/2006 |
| WO | WO2007065538 | 6/2007 |
| WO | WO2007110790 A1 | 10/2007 |
| WO | WO2007125216 A1 | 11/2007 |
| WO | WO2008017484 A1 | 2/2008 |
| WO | WO2008028278 A1 | 3/2008 |
| WO | WO2008034549 | 3/2008 |
| WO | WO2008035101 | 3/2008 |
| WO | WO2008035101 A2 | 3/2008 |
| WO | WO2008035101 A3 | 3/2008 |
| WO | WO2008060130 | 5/2008 |
| WO | WO2008061658 | 5/2008 |
| WO | WO2008068683 | 6/2008 |
| WO | WO2008085446 A2 | 7/2008 |
| WO | WO2008088827 A2 | 7/2008 |
| WO | WO2008125884 | 10/2008 |
| WO | WO2008157847 | 12/2008 |
| WO | WO2009000097 A2 | 12/2008 |
| WO | WO2009023731 | 2/2009 |
| WO | WO2009026949 | 3/2009 |
| WO | WO2009083521 A2 | 7/2009 |
| WO | WO2009083521 A3 | 7/2009 |
| WO | WO2009085058 | 7/2009 |
| WO | WO2009090648 | 7/2009 |
| WO | WO2009113910 | 9/2009 |
| WO | WO2009113910 A1 | 9/2009 |
| WO | WO2009128012 | 10/2009 |
| WO | WO2009132342 | 10/2009 |
| WO | WO2010046238 A1 | 4/2010 |
| WO | WO2010059366 | 5/2010 |
| WO | WO2010147868 | 12/2010 |
| WO | WO2011023582 A2 | 3/2011 |
| WO | WO2011036048 A1 | 3/2011 |
| WO | WO2011039630 A1 | 4/2011 |
| WO | WO2011117424 | 9/2011 |
| WO | WO2011151169 A1 | 12/2011 |
| WO | WO2011151171 A1 | 12/2011 |
| WO | WO2011151172 | 12/2011 |
| WO | WO2012018519 | 2/2012 |
| WO | WO2013083595 | 6/2013 |

OTHER PUBLICATIONS

Botelho et al., Antimicrobial activity of the essential oil from Lippia sidoides, carvacrol and thymol against oral pathogens, Brazilian Journal of Medical and Biological Research, 2007, 349-356, 40, ., .

Burt et al, Essential oils: their antibacterial properties and potential application in foods—a review, Int J of Food Microbiology, 2004, 223-253, 94.

Davies A., Action of Biguanides, Phenols and detergents on *Escherichia coli* and its spheroplasts, Action of Biguanides, 1969, 233-243, 32.

Dimitrijevic, et al., A study of the synergistic antilisterial effects of a sub-lethal dose of lactic acid and essential oils, Food Chemistry, Jan. 1, 2007, 774-782, 104, Elsevier, US.

Friedman, et al., Antibacterial Activities of Naturally Occurring Compounds Against Antibiotic-Resistant Bacilllus cereus, Journal of Food Protection, Mar. 12, 2004, 1774-1778, 67, No. 8. Journal of Food Protection, US.

Gablin, Balsamic fragrances Lemon thyme, Handmade Soaps, Jul. 18, 2007, 84, ., RU.

Hong S. Antimicrobial Activity of Tyramine Derivatives, Antimicrobial Activity of Tyramine Derivatives, Oct. 29, 2000, NA, NA.

Karabit et al. Studies on the evaluation of preservative efficacy III. The determination of antimicrobial characteristics of benzalkonium chloride, Int J of Pharmaceutics, 1988, 141-147, 46.

Kubo et al, Antimicrobial activity of anethole and related compounds from aniseed, Journal of the Science of Food and Agriculture, 2008, 242-247, 88.

Mah J H, *Paenibacillus tyraminigenes* sp. nov. isolated from Myeolchi-jeotgal. a traditional Korean salted and fermented anchovy, *Paenibacillus tyraminigenes* sp. nov. isolated from Myeolchi-jeotgal., Oct. 31, 2008, pp. 209-214, vol. 127. No. 3.

Oyedemi et al , The proposed mechanism of bactericidal action of eugenol, a-terpineol and y-terpinene against listeria monocytogened, streptococcus pyogenes, proteurs vulgaris and *Escherichia coli*, African Journal of Biotechnology, Apr. 6, 2009, 1280-1286, 8(7).

Sato et al, Antimicrobial effect of trans-cinnamaldehyde, (−)-perillaldehyde, (−)-citronellal. citral, eugenol and carvacrol on airborne microbes using an airwasher, Biol Pharm bull, 2006, 2292-2294, 29(11).

Tippayatum et al, Antibacterial activities of thymol, eugenol and nisin against some food spoilage bacteria, Nat Science, 2007, 319-323, 41.

Van Der Wolf, Disinfection of vegetable seed by treatment with essential oils, Seed Science and Technology, 2008, 76-88, 36, US.

Zhigzhitzhapova, Chemical composition of an essential oil of Baikal thyme, Vegetable feed chemistry, 2008. 73-76, No. 1, RU.

Zhigzhitzhapova, The Chemical Composition of the Essential Oil of Baikal Thyme, Vegetable fee chemistry, 2008, 73-76, 1, RU.

Henkel Oppositon on Application No. 2 348 838 B1 dated Feb. 7, 2014.

Biersdorf Oppositon on Application No. 2 348 838 B1 dated Feb. 6, 2014.

PCT International Search Report and Written Opinion on Application No. PCT/EP2010/062982 dated Dec. 28, 2010.

PCT International Search Report PCT International Search Report on Application No. PCT/EP2010/062982 dated Dec. 28, 2010on Application No. PCT/EP2012/070369 dated Jun. 17, 2013.

(56) References Cited

OTHER PUBLICATIONS

PCT International Search Report on Application No. PCT/EP2009/063081 dated Jan. 25, 2010.
PCT International Search Report on Application No. PCT/EP2012/073193 dated Mar. 18, 2013.
PCT International Search Report on Application No. PCT/EP2013/054333 dated May 8, 2014.
PCT International Search Report on Application No. PCT/EP2013/066144 dated Oct. 30, 2013.
European Search Report on Application No. EP 13 15 2865 dated Aug. 1, 2013.
European Written Opinion on Application No. EP 10 747 899 dated Jan. 22, 2013.
European Search Report on Application No. EP 09 15 3930 dated Jul. 27, 2009.
European Search Report on Application No. EP 12 18 3546 dated Jan. 16 2013.
European Search Report on Application No. EP 12 16 8864 dated Aug. 13, 2012.
European Search Report on Application No. EP 12 15 2564 dated Aug. 27, 2012.
Castor Oil, Wikipedia (website),1-4, US.
A. Perez-Vasquez et al., Antimicrobial activity and chemical composition of the essential oil of Hofineisteria schaffneri, Journal of Pharmacy and Pharmacology, Aug. 5, 2010, 579-586, vol. 63.
Abdeslam Jaafari, Hassan Ait Mouse, El Mostapha Rakib et al, Chemical composition and antitumor activity of different wild varieties of Moroccan thyme, Brazilian Journal of Pharmacognosy, Aug. 27, 2007, 477-491, 17 (4).
Budavari (Editor), An Encyclopedia of Chemicals, Drugs, and Biologicals, The Merck Index, 1996, 1568, 12th Edition: Merck Research Laboratories, Whitehouse Station, US.
Cen Members, Chemical disinfectants and antiseptics—Quantitative suspension test for the evaluation of bactericidal activity of chemical . . . , European Standard, Jan. 1, 1997, 1-18, EN 1276.
Coco et al., Candida biofilms in denture stomatitis: novel detection and treatment methods, The Pan European Federation of the Internatnional Association for Dental Research, Sep. 11, 2008, ., ., ., .
Evandro Leite De Souza, Interference of heating on the antimicrobial activity and chemical composition of Origanum vulgare L. (Lamiaceae) essential oil, Interference of heating on the antimicrobial activity and chemical composition of Origanum vulgate L. (Lamiaceae) essential oil, Apr. 1, 2008, 1-7, vol. 28, No. 2.
Figueredo et al, Studies of mediterranean oregano populations. VIII-Chemical composition of essential oils of oreganos of various origins, Flavour and Fragrance Journal, May 9, 2005, 134-139, 21.
Gablin, Balsamic fragrances Lemon thyme, Handmade Soaps, Jul. 18, 2007. 84, RU.
Jalali-Heravi et al, Analysis of Iranian rosemary essential oil: application of gas chromatography—mass spectrometry combined with chemometrics, Journal of Chromatography A, Mar. 21, 2011, 2569-2576, 1218.
Kirchner et al, Chemical composition and antimicrobial activity of Hedyosmum brasiliense Miq., Chloranthaceae, essential oil, Brazilian Journal of Pharmacognosy, Jan. 11, 2010, 692-699, 20(5).
Kisgyorgy et al, Essential oil of the more important indigenous *Thymus* species occurring in the composition of Serpylli herba, Farmakognoziai Tansz., Jan. 1, 1983, 124-130, 29.
Leung A Y; Foster, Encyclopedia of common and natural ingredients used in food, drugs and cosmetics, Cinnamon (and Cassia), Jan. 1, 1996, pp. 167-170,260-264,393-397,405-408,492-494,510-511; ISBN: 978-0-471-50826-7.
M. 5ebesan, Analysis of the I,II Essential Oils from Thyme (Thymus vulgaris L) and from Peppermint (Mentha piperita L), Analysis of the I,II Essential Oils from Thyme and from Peppermint, Dec. 31, 2008, 212-214, Retrieved from the Internet.
Majnooni et al, Chemical composition, cytotoxicity and antioxidant activities of the essential oil from the leaves of citrus aurantium L., African Journal of Biotechnology. May 1, 2012. 498-503, 11(2).

Miladinovie et al, Investigation of the chemical composition—antibacterial activity relationship of essential oils by chemometric methods, Anal Bioanal Chem, Mar. 3, 2012, 1007-1018, 403.
Mintel, Antibacterial Fluride Toothpaste, Antibacterial Fluride Toothpaste, Nov. 2007. NA, NA, NZ.
Mintel, Mouth Rinse, Mouth Rinse, Oct. 2007, NA, NA, GB.
Naigre Ruth, Comparison of antimicrobial properties of monoterpenes and their carbonylated products, Comparison of antimicrobial properties of monoterpenes and their carbonylated products, 1996, 275-277, vol. 62, No. 3.
Rossi et al, Chemical fingerprinting and bioactivity of Amazonian Ecuador croton lechleri Mull. Arg. (Euphorbiaceae) stem bark essential oil: A new functional food ingredient?, Food Chemistry, Jun. 1, 2011, 837-848, 126.
Sagoo SK, Chitosan potentiates thE antimicrobial action of sodium benzoate on spoilage yeasts, Chitosan and Benzoate, Jan. 3, 2008, 168-172, 34—No. 3.
Sawamura et al. Characteristic odor components of citrus reticulata blance (Ponkan) cold-pressed oil, Biosci. Biotechnol. Biochem., Apr. 16, 2004, 1690-1697, 68(8).
Shixiang, Anticorrosive functions of convention flavors and fragrances, Toothpaste industry, 2000, 23-27, 2, CN.
Singh et al. Antioxidant and antimicrobial activities of essential oil and various oleoresins of Elettaria cardamomum (seeds and pods), Journal of the Science of Food and Agriculture, Mar. 6, 2007, 280-289, 88.
Tian et al, Chemical composition and antifungal activity of essential oil from cicuta virosa L. var. latisecta celak, International Journal of Food Microbiology, Jan. 1, 2011, 464-470, 145.
Umback et al., Georg Thieme Verlag, Kosmetik, 1995, 360-369, ., DE.
Wang, Synergistric Antimicrobial Activities of Natural Oils with Chitosan Films, Journal of Agricultural and Food Chemistry, Oct. 29, 2011, 12411-12419, vol. 59 No. 23, ACS Publications, US.
Younhee Byun et al., Analysis of Composition and Activity of Essential Oil from Chrysanthemum zawadskii var. latilobum and C. indicum against Antibiotic-Resistant Pathobenic Bacteria, Natural Product Sciences, Jun. 16, 2008, 138-142, vol. 14-No. 2.
Yu et al., Chemical composition and antimicrobial activity of the essential oil of Scutellaria barbata, Phytochemistry 65 (2004), Sep. 5, 2003, 881-884, 65.
Zrira et al, Chemical composition of the essential oil of nine eucalyptus species growing in Morocco, Flavour and fragrance journal, Apr. 2, 2004, 172-175, 19.
Aas et al, Defining the Normal Bacterial flora of the Oral Cavity, Journal of Clinical Microbiology, 2005, pp. 5721-5732, 43, 11, US.
Baratta et al., Chemical Composition, Antimicrobial & Antioxidative Activity of Laurel, Sage, Rosemary, Oregano Coriander Essential Oils, Journal of Essential Oil Research, Jan. 1, 1998, pp. 618-627, vol. 10, No. 6, GB.
Bechtold et al, Extraction of natural dyes for textile dyeing from coloured plant wastes relased from the food and beverage industry, Journal of the Science of Food and Agriculture 2006 vol. 86 p233-242 Abstract, Nov. 14, 2005, pp. 233-242, 86.
Bechtold et al, Extraction of natural dyes for textile dyeing from coloured plant wastes released from the food and beverage industry, Journal of the science of food and agriculture 2006 vol. 86 p233-242, Nov. 14, 2005, pp. 233-242, 86.
Biondi et al., Antimicrobial Activity & Chemical Composition of Essential Oils from Sicilian Aromatic Plants, Flavour Fragrance Journal, Jan. 1, 1993, pp. 331-337, v. 8, No. 6, IT.
Burger et al., Mammalian Exocrine Secretions. XII: Constituents of Interdigital Secretions of Bontebok, Damaliscus dorcas dorcas, and Blesbok, D.d. phillipsi, Journal of Chemical Ecology, 1999, pp. 2057-2084, vol. 25, No. 9.
Cao et al., Essential oil composition, antimicrobial and antioxidant properties of Mosla chinensis Maxim, Food Chemistry, Jan. 1, 2009, pp. 801-805, vol. 115, CN.
Christoph et al., Glycerol, Ullmann's Encyclopedia of Industrial Chemistry, 2012, pp. 67-82. NB: only relevant pp. 67-69 and 79, vol. 17, Wiley-VCH Verlag GmbH & Co. KGaA, Weinheim.
Cimanga et al., Chemical Composition & Antifungal Activity of Essential Oils of Some Aromatic Medicinal Plants Growing in the

(56) References Cited

OTHER PUBLICATIONS

Democratic Republic of Congo, Journal of Essential Oil Research, Jan. 1, 2002, pp. 382-387, vol. 14, No. 5, BE.
Claudia Juliano et al., Composition and in vitro Antimicrobial Activity of the Essential Oil of Thymus herba-barona Loisel Growing Wild in Sardinia, J. Essent. Oil Res., 2000, pp. 516-522, vol. 12.
Cosentino et al., In-vitro antimicrobial activity and chemical compoistion of Sardinian Thymus essential oils, Letters in Applied Microbiology, 1999, pp. 130-135, vol. 29.
Darwish et al., Effects of Hydrotropic Agents on the Solubility, Precipitation, and Protein Binding of Etoposide, Journal of Pharmaceutical Sciences, 1989, pp. 577-581, vol. 78 No. 7.
Encyclopedia of Chinese Chemical Products, Jan. 31, 2005, p. 149; with abstract., vol. 1, Chemical Industry Press, CN.
Faith Demirci et al., Investigation of the Origanum onites L. Essential Oil Using the Chorioallantoic Membrane (CAM) Assay, Journal of Agricultural and Food Chemistry, 2004, pp. 251-254, vol. 52.
G. Taillandier et al., QSAR analysis of a series of antimicrobial phenols by means of the .SIGMA.D and .SIGMA.S parameters, Pharmazie, 1987, pp. 538-540, vol. 42, No. 8.
Goren et al., The Chemical Constituents & Biological Activity of Essential Oil of Lavandula stoechase ssp stoechas, Journal of Biosciences, Jan. 1, 2002, pp. 797-800, v. 57, TR.
Ho et al., Composition & Bioactivities of the Leaf Essential Oils of Cinnamomum subavenium Miq. form Taiwan, Journal of Essential Oil Research, Jan. 1, 2008, pp. 328-334, v. 20, No. 4, TW.
IPRP in PCTEP2012073193, Mar. 28, 2014.
IPRP in PCTEP2012074399, Jul. 10, 2014, pp. 1-20, WO.
IPRP2 in PCTEP2011057953, Oct. 25, 2012.
IPRP2 in PCTEP2011070093, Mar. 22, 2013.
IPRP2 in PCTEP2011070314, Apr. 5, 2013, WO.
IPRP2 in PCTEP2012073005, Apr. 9, 2014.
IPRP2 in PCTEP2012074416, Jul. 10, 2014.
Jirovetz et al., Analysis of the essential oil volatiles of Douglas fir (*Pseudotsuga menziesii*) from Bulgaria, Flavour & Fragrance Journal, Jan. 1, 2000, pp. 434-437, vol. 15, No. 6, AT.
Joulain et al., The Absolute From flowers of Jasminum auriculatum Vahl from India, Flavour and Fragrance Journal, 1995, pp. 193-197, vol. 1.
Keller et al., Occurrence of virulence-Associated properties in Enterobacter cloacae, Infection and Immunity, 1998, pp. 645-649, 66, 2, US.
Kurita et al., Antifungal Activity of Components of Essential Oils, Agric. Biol. Chem., 1981, pp. 945-952, vol. 45 No. 4.
Mintz et al., Correlation of Minimum Inhibitory Concentrations Toward Oral Bacterial Growth Based on the Abraham Model, QSAR & Combinatorial Science, 2006, pp. 912-920, vol. 25.
Mohammad Nazrul Islam Bhuiyan et al., Essential oils analysis of the rhizomes of Alpinia conghigera Griff. and leaves of Alpinia malaccensis (Burm.f.) Roscoe from Bangladesh, African Journal of Plant Science, 2010, pp. 197-201, vol. 4 No. 6, Academic Journals.
Moolla et al., The Biological Activity & Essential Oil Composition of 17 Agathosma (Rutaceae) Species, Journal of Essential Oil Research, Jan. 1, 2006, pp. 2-16, v. 18, ZA.
Muhammad Ashraft et al., Composition of Leaf Essential Oil of Eucalyptus camaldulensis, Asian Journal of Chemistry, 2010, pp. 1779-1786, vol. 22 No. 3.
Nazer et al., Combinations of food antimicrobials at low levels to inhibit the growth of Salmonella sv. Typhimurium: a synergistic effect?, Food Microbiology, 2005, pp. 391-398, vol. 22 Issue 5.
Nguyen Truc Linh et al., Study of the Essential Oil of Limnophila Rugosa (Roth.) Merr. in the South of Vietnam, Journal of Essential Oil Bearing Plants, 2011, pp. 366-372, vol. 14 No. 3.
Notice of Opposition (Biersdorf) in EP2348838 (09783843), Feb. 6, 2014.
Notice of Opposition (Henkel) in EP2348838 (09783843), Feb. 7, 2014.
Notice of Opposition in EP12799125 (EP2787827), Aug. 19, 2016.
Peleg et al., Bitterness and astringency of flavan-3-ol monomers, dimers and trimers, Journal of the Science of Food and Agriculture, Jan. 1, 1999, 1123-1128, 79.
Satpathy et al., Preliminary evaluation of nutraceutical and therapeutic potential of raw Spondias pinnata K., an exotic fruit of India, Food Research International, 2011, pp. 2076-2087, vol. 44, Elsevier.
Schmidt, Claus Oliver et al, Antimicrobial mildew-resistant coating, Coatings Technology & Abstracts, 2005, p. 49 (Original & abstract in English only), 3.
Search Report & Written Opinion in EP15198664, Feb. 9, 2016.
Sivropoulou et al., Antimicrobial Activity of Mint Essential Oils, Journal of Agricultural and Food Chemistry, 1995, pp. 2384-2388, vol. 43, No. 9.
Summons in EP09783843 (EP2348838), Jun. 19, 2015.
Takeshi Deyama Etc., Studies on the Components of Essential Oil of Clove, Yakugaku Zasshi (Abstract), 1971, pp. 1383-1386, 91(12).
The Cosmetic, Toiletry, And Fragrance Association, Monographs, International Cosmetic Ingredient Dictionary and Handbook, 2008, pp. 1-5; pp. 2734, 2757-2758, vol. 3 12th Edition, US.
Walter Feldheim, Investigation of the presence and significance of theanine in the tea plant, Investigation of the presence and significance of theanine in the tea plant, Jan. 1, 1986, 537-534, 37-6.
Wei Wende (Ed.), Cyclopedia of Organic Chemical Materials, Cyclopedia of Organic Chemical Materials, 1999, p. 935 (and Cover Page)—in Chinese only, no Engl abstract or translation available, vol. II (Second Edition).
Written Opinion in EP12168864, Aug. 13, 2012.
Written Opinion in EP09175200, Feb. 8, 2010, EP.
Written Opinion in EP11151946, Jul. 7, 2011, EP.
Written Opinion in EP11784639, Jun. 21, 2016.
Written Opinion in EP12150935, May 15, 2012.
Written Opinion in EP12150937, May 4, 2012, EP.
Written Opinion in EP12151770, Aug. 2, 2012, EP.
Written Opinion in EP12152561, Aug. 27, 2012.
Written Opinion in EP12152564, Aug. 27, 2012.
Written Opinion in EP12183546, Jan. 16, 2013.
Written Opinion in EP12794989, Jun. 1, 2015, EP.
Written Opinion in EP12797891, Jun. 1, 2015, EP.
Written Opinion in EP12798329, Jul. 24, 2015, EP.
Written Opinion in EP12798699, Dec. 11, 2015.
Written Opinion in EP13152865, Aug. 1, 2013.

LIQUID PERSONAL WASH COMPOSITION

TECHNICAL FIELD

The invention relates to a liquid personal cleaning composition. The invention more particularly relates to a personal cleaning composition that provides synergistic antimicrobial efficacy.

BACKGROUND OF THE INVENTION

Liquid compositions for personal washing applications have been known. Such compositions include hand washing liquids usually dispensed from bottles provided with a hand pump which is actuated by pressing with the hand. Such kind of hand washing liquids are also dispensed in public places like bathrooms in airports, hotels, restaurants and offices. Other personal cleaning liquids include facewash liquids, bodywash liquids, shampoos and hair conditioners.

Such compositions are used not only to clean the surface of the body to give the consumer of feeling of being clean of dust, sebum, and sweat but also give the consumer a satisfaction of having disinfected the surface to be free of disease causing germs. Liquid forms of such compositions are known for personal care. Such compositions include antimicrobial actives that specifically target microorganisms like bacteria and virus to either kill or inactive them.

Sanitizing and disinfecting soap compositions comprising chlorine-based antimicrobial agent such as triclosan are known. Such compositions require rather long contact time to provide efficacious antimicrobial action. In practice, users, in particular children, do not spend long time in cleaning and as a result, cleaning with such compositions does not provide adequate prevention from surface or topical infection or adequate protection against diseases. The user, in spite of cleaning hands, is likely to have skin with relatively inadequate bacterial removal and may cause contamination of further animate and/or inanimate surfaces that may lead to spreading of pathogens and consequent diseases. Users in general and children in particular who wash contaminated hands before meals with slow-acting antimicrobial compositions for relatively short time are at risk of contacting diseases. These short time scales of cleaning action are ineffective in providing the desired benefit since most known antimicrobials commonly used in such products take several hours to provide the desired kill of microbes.

Therefore, the present applicant realized the need for providing a composition that gives relatively more efficacious antimicrobial action when cleaning period is relatively small, typically about 5 minutes or less, preferably lesser than 2 minutes and in many cases less than one minute or sometimes as low as 15 seconds or lesser. They have, in a prior patent application published as WO2010046238 disclosed a novel combination of thymol and terpineol that interact synergistically to enable fast antimicrobial action in less than about 15 seconds. The present inventors have found that inclusion of selected di or tricarboxylic acid or a salt thereof, when combined with thymol or terpineol provide similar synergistic antimicrobial action in a rapid fashion and such efficacy is obtained at much lower concentrations of thymol and/or terpineol. This invention has the advantage that essential oil actives like terpineol and thymol have a strong medicinal odour which is not liked by some consumers and it is advantageous to include thymol and terpineol at lower concentrations while ensuring the same efficient anti-microbial action. Further, it has been found by way of the present invention that inclusion of select anionic surfactants aids in further enhanced antimicrobial efficacy.

Liquid personal cleaning compositions are known. US2008045491 (Fitchmun) discloses a non-toxic antimicrobial surface sanitizer composition comprising a water-miscible alcohol, water, a weak acid and a multivalent cation (e.g. metal ion or metal compound). The composition may also include one or more of an emollient, oxidative agent, humectant, lubricant, plant-derived alkene, antimicrobial component or plant-derived essential oil can be formulated as solutions for sanitizing hard surfaces such as countertops and floors, or as solutions/gels for application to animal skin.

The above publication utilizes the well known antimicrobial efficacy of alcohol which is much stronger than most other known antimicrobial actives. Many consumers do not prefer to use products that utilize alcohol as they consider it as harsh on the skin and so it is desirable to develop new combination of actives that provide similar or better antimicrobial efficacy in much rapid time frame while utilizing actives that are considered mild on skin.

US2006093570 (Reckitt Benckiser) describes a surface treatment composition, preferably for personal use, comprising at least one surfactant and at least two different organic acids and/or salts or organic acids, and wherein the total concentration of the organic acids and/or salts in the composition is at least 0.5 percent (w/v). The invention further extends to a method of treating a surface, preferably hair or skin, to remove dirt and to remove or inhibit microbial growth.

The patent publication cited above does not address the problem of slow-acting antimicrobial composition, nor disclose the synergistic combination of actives disclosed and claimed in the present invention for the fast acting antimicrobial action in cleaning and disinfecting skin and/or other keratinous substrates of humans and/or animals.

It is an object of the present invention to overcome or ameliorate at least one of the disadvantages of the prior art, or to provide a useful alternative.

Another object of the present invention is to provide a liquid personal care cleaning and disinfecting composition that has relatively fast antimicrobial action.

SUMMARY OF THE INVENTION

According to the first aspect of the present invention there is provided a liquid personal cleaning composition with a pH in the range of 4.5 to 7.5 comprising less than 1% C1 to C3 alcohol comprising
  (a) 0.25 to 2.5% by weight of di or tri carboxylic acid or a salt thereof;
  (b) 0.01 to 2% by weight thymol;
  (c) 0.01 to 2% by weight terpineol; and
  (d) 70 to 90% by weight water.

According to another aspect of the present invention there is provided a method of disinfecting the external surface of an animal or human body comprising the steps of contacting the surface with a composition as claimed in any one of the preceding claims followed by the step of rinsing the surface with water or wiping the surface to be substantially free of the composition.

DETAILED DESCRIPTION OF THE INVENTION

These and other aspects, features and advantages will become apparent to those of ordinary skill in the art from a reading of the following detailed description and the appended claims.

For the avoidance of doubt, any feature of one aspect of the present invention may be utilised in any other aspect of the invention. The word "comprising" is intended to mean "including" but not necessarily "consisting of" or "composed of". In other words, the listed steps or options need not be exhaustive. It is noted that the examples given in the description below are intended to clarify the invention and are not intended to limit the invention to those examples per se. Similarly, all percentages are weight/weight percentages unless otherwise indicated.

Except in the operating and comparative examples, or where otherwise explicitly indicated, all numbers in this description indicating amounts of material or conditions of reaction, physical properties of materials and/or use are to be understood as modified by the word "about". Unless specified otherwise, numerical ranges expressed in the format "from x to y" are understood to include x and y. When for a specific feature multiple preferred ranges are described in the format "from x to y", it is understood that all ranges combining the different endpoints are also contemplated.

By a personal cleaning composition as used herein, is meant to include a composition for cleaning and disinfecting topical areas e.g. skin and/or hair of mammals, especially humans. Such a composition may be generally classified as leave-on or rinse off, and includes any product applied to a human body for also improving appearance, cleansing, odor control or general aesthetics. It is more preferably a rinse off product. The composition of the present invention in the form of a liquid but may be modified to include a lotion, cream, foam or gel, or toner, or applied with an implement or via a face mask, pad or patch. "Skin" as used herein is meant to include skin on the face and body (e.g., neck, chest, back, arms, underarms, hands, legs, buttocks and scalp). The composition of the invention is also of relevance to applications on any other keratinous substrates of the human body other than skin e.g. hair where products may be formulated with specific aim of providing disinfection and cleaning.

The first aspect of the invention provides for a liquid personal cleaning composition with a pH in the range of 4.5 to 7.5 comprising less than 1% C1 to C3 alcohol comprising di or tri carboxylic acid or a salt thereof, thymol, terpineol and water.

The composition has a pH in the range of 4.5 to 7.5. The composition provides antimicrobial efficacy even without any contribution in such efficacy from low molecular weight alcohols viz. C1 to C2 alcohols e.g. methanol, ethanol, proponol or isopropyl alcohol which are usually water miscible.

If present, they may be less than 1% by weight of the composition, preferably less than 0.5%, more preferably less than 0.1% and optimally absent from the composition. The composition comprises 0.25 to 2.5%, preferably 0.5 to 2%, more preferably 0.75 to 1.25% by weight of the composition di or tri carboxylic acid or a salt thereof.

The di or tri carboxylic acid is preferably chosen from an oxalic, fumaric, phthalic, maleic, malic, malonic or citric acid. The di or tricarboxylic acid is most preferably a malic, malonic, or citric acid. It is possible that the part of the di or tricarboxylic acid that is added to prepare the composition of the invention is present as salt of the di or tricarboxylic acid depending on the pH at which the composition is formulated. In such cases, the salt is preferably alkali metal or alkaline earth metal salts, more preferably alkali metal salts of which sodium salt is most preferred. Structure of salts of some of the carboxylic acids are given below:

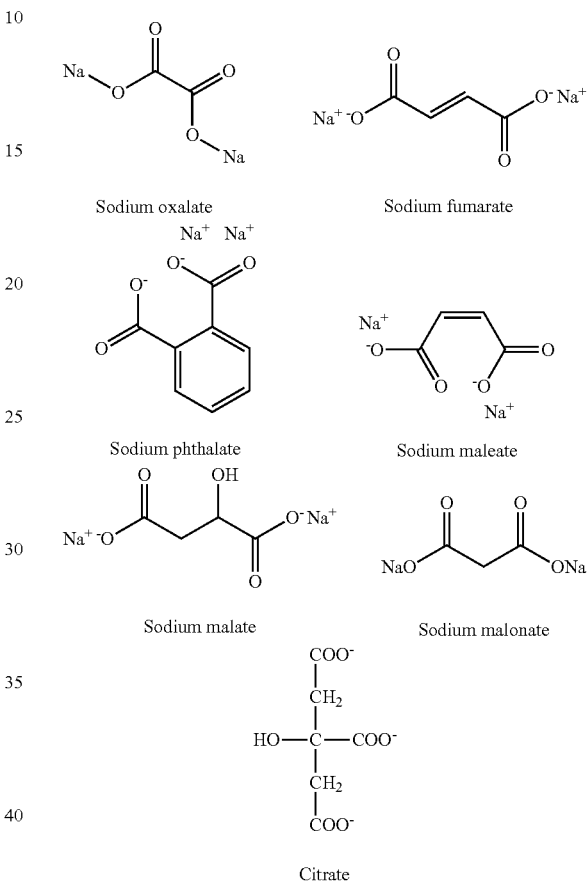

It is observed that inclusion of di or tri carboxylic acid in the composition of the invention provides for the desired antimicrobial efficacy while mono carboxylic acids do not demonstrate as good an efficacy.

The composition comprises a combination of essential oil antimicrobial actives thymol and terpineol at 0.01 to 2% by weight of the composition of each active.

Thymol is preferably present in 0.02 to 0.5%, more preferably up to 0.3% by weight, further more preferably up to 0.2% by weight of the composition. Thymol may be added to the antimicrobial composition in purified form. Alternatively, thyme oil or thyme extract comprising thymol may be added to the antimicrobial composition, while ensuring that thymol is present in the desired concentration in the composition of the present invention. Thyme oil or thyme extract is obtained from the thyme plant. Thyme plant refers to a plant belonging be genus *Thymus* and includes but is not limited to the following species: *Thymus vulgaris, Thymus zygis, Thymus satureoides, Thymus mastichina, Thymus broussonetti, Thymus maroccanus, Thymus pallidus, Thymus algeriensis, Thymus serpyllum, Thymus pulegoide*, and *Thymus citriodorus*.

The structures of thymol and its isomer carvacrol are given below:

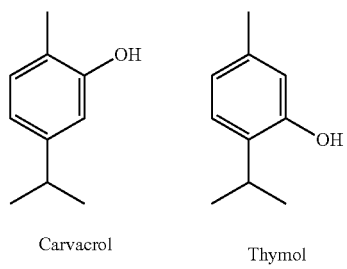

Carvacrol    Thymol

Preferred antimicrobial compositions of the present invention have terpineol in 0.05 to 1% more preferably up to 0.5% by weight of the composition. The terpineol is preferably selected from alpha-terpineol, beta-terpineol, gamma-terpineol or mixtures thereof. It is particularly preferred that the terpineol is alpha-terpineol. Terpineol may be added to the antimicrobial composition in purified form. Alternatively pine oil comprising terpineol may be added to the antimicrobial composition.

The structure of a terpineol compound is given below:

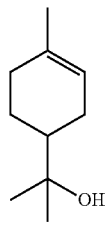

The composition of the invention comprises water as a preferred carrier. Water is present in 70 to 90%, preferably 85 to 90% by weight of the composition.

The composition of the invention optionally comprises a surfactant. Preferred surfactant is an anionic surfactant. Anionic surfactant is preferably present in 0.5 to 15%, more preferably 1 to 5% by weight of the composition. Particularly preferred anionic surfactants are glycinates, alkyl sulphates or ethoxylated alkyl sulphates.

The composition may further comprise various additional ingredients known to a person skilled in the art. Such additional ingredients include but are not limited to: perfumes, pigments, preservatives, emollients, sunscreens, emulsifiers, gelling agents, or thickening agents.

The antimicrobial composition may be in form of a liquid but the liquid composition may be further thickened to a gel or a paste. The antimicrobial composition of the present invention can be used for cleansing and care of human skin and hair.

According to another aspect of the present invention there is provided a method of cleaning and disinfecting a keratinous substrate of human and/or animals comprising applying to said surface a composition of the invention followed by a step of rinsing or wiping the surface to be substantially free of the composition. The composition is preferably diluted with water in a weight ratio of 1:10 to 1:40, preferably in a ratio of 1:20 to 1:30, before or during the step of applying the composition on the surface.

The method preferably comprises a step of rinsing the surface with a suitable solvent preferably water or the surface may be wiped with a suitable wipe.

The inventors have determined that the composition of the invention provides an antimicrobial action where the contact time of the antimicrobial actives with the surface is low, i.e. of the order of less than 5 minutes, preferably less than 2 minutes, further more preferably less than a minute and in many cases less than 15 seconds.

The invention will now be demonstrated by way of the following non-limiting examples.

EXAMPLES

Example 1 to 9

Compositions as shown in Table-1 were prepared and tested for antibacterial efficacy using the following test protocol.

Protocol: Contact kill Assay (15 second contact kill) The test bacteria *E.coli* ATCC 10536 was grown overnight in TSB broth (Difco-30 gpl) at 37° C. for 16 hours. 2 ml of this was sub-cultured in 40 ml of fresh TSB broth and kept to grow for 4 hours at 37° C. Then the culture was processed by spinning at 2057 g for 5 minutes, washing twice and collecting the cells.

The cell density was adjusted at 620 nm to get the final count of $10^8$ cfu/ml (0.8 OD). The compositions as shown in Table-1 were prepared and kept for 3 hours for maturation.

9 ml of the compositions was taken in a sample container and 1 ml of processed culture was added to it. After a 15 second contact time, 1 ml of the above mixture was immediately neutralized in D/E broth (Difco-39 gpl). Serial dilution was done in D/E broth and plated on TSA (Difco-40 gpl) in duplicates. In case of the control, 1 ml of test culture was added to 9 ml of saline and was serially diluted and plated on TSA. After solidification, the plates were incubated at 37° C. for 48 hrs. The residual colonies were counted after 48hrs of incubation and the efficacy was determined by comparing with control. The data is summarized in Table-1 below.

TABLE 1

| Examples | Thymol (wt %) | Terpineol wt % | Di/tri Carboxylic Acid | Di/tri carboxylic acid (wt %) | pH | Log reduction |
|---|---|---|---|---|---|---|
| Example 1 | 0.2 | 0.5 | — | — | 6.9 | 7.2 |
| Example 2 | 0.025 | 0.0625 | — | — | 6.9 | 0 |
| Example 3 | 0.025 | 0.0625 | Malic acid | 1.0 | 5.0 | 7.2 |
| Example 4 | 0.025 | 0.0625 | Malic acid | 1.0 | 7.3 | 6.1 |
| Example 5 | 0.025 | 0.0625 | Malonic acid | 1.0 | 5.0 | 7.2 |
| Example 6 | 0.025 | 0.0625 | Malonic acid | 1.0 | 7.3 | 6.3 |
| Example 7 | 0.025 | 0.0625 | Citric acid | 1.0 | 5.0 | 7.2 |
| Example 8 | 0.025 | 0.0625 | Citric acid | 1.0 | 7.2 | 6.5 |
| Example 9 | — | — | Malonic acid | 1.0 | 5.0 | 0 |
| Example 10 | — | — | Citric acid | 1.0 | 5.0 | 0 |

The data in Table-1 indicates that when di or tri carboxylic acid are combined with low concentrations of essential oil actives (thymol and terpineol) they provide synergistic antibacterial efficacy (Examples 3 to 8) as compared to compositions outside the invention (Example 2, 9 and 10).

The invention claimed is:
1. A liquid personal cleaning composition with a pH in the range of 4.5 to 7.5 comprising less than 1% C1 to C3 alcohol consisting essentially of
   (a) 0.25 to 2.5% by weight di or tri carboxylic acid or a salt thereof;
   (b) 0.02 to 0.2% by weight thymol;
   (c) 0.05 to 0.5% by weight terpineol; and
   (d) 70 to 90% by weight water.

2. A composition as claimed in claim 1 wherein said di or tri carboxylic acid is chosen from an oxalic, fumaric, phthalic, maleic, malic, malonic or citric acid.

3. A composition as claimed in claim 2 wherein said di or tricarboxylic acid is chosen from a malic, or citric acid.

4. A composition as claimed in claim 1 comprising an anionic surfactant.

5. ) A composition as claimed in claim 4 wherein said anionic surfactant is present in an amount of 0.5 to 15% by weight of the composition.

6. A composition as claimed in claim 4 wherein said anionic surfactant is chosen from a glycinate, alkyl sulphate or ethoxylated alkyl sulphate.

7. A method of disinfecting the external surface of an animal or human body comprising the steps of contacting the surface with a composition as claimed in any one of the preceding claims followed by the step of rinsing the surface with water or wiping the surface to be substantially free of the composition.

* * * * *